US00PP16746P3

(12) United States Plant Patent
Wang

(10) Patent No.: US PP16,746 P3
(45) Date of Patent: Jul. 4, 2006

(54) *DENDROBIUM PLANT NAMED 'YFY-HS1'*

(50) Latin Name: *Dendrobium tosaense×Dendrobium huoshanese*
Varietal Denomination: YFY-HS1

(75) Inventor: Lih-Hwa Wang, Taipei (TW)

(73) Assignee: Yuen Foong Yu Paper Mfg. Co., Ltd. (TW)

( * ) Notice: Subject to any disclaimer, the term of this patent is extended or adjusted under 35 U.S.C. 154(b) by 122 days.

(21) Appl. No.: 10/943,358

(22) Filed: Sep. 17, 2004

(65) Prior Publication Data

US 2006/0064791 P1 Mar. 23, 2006

(51) Int. Cl.
*A01H 5/00* (2006.01)

(52) U.S. Cl. ..... Plt./311

(58) Field of Classification Search ..... Plt./311
See application file for complete search history.

*Primary Examiner*—Anne Marie Grunberg
*Assistant Examiner*—June Hwu
(74) *Attorney, Agent, or Firm*—Mathews, Shepherd, McKay & Bruneau, P.A.

(57) ABSTRACT

A new and distinct variety of *Dendrobium* plant named 'YFY-HS1' is provided. The plant is characterized by having a great growth vigor and the extract of "DCMPbL6, 7D2H2" defined in U.S. patent application Ser. No. 10/648,651.

6 Drawing Sheets

Botanical classification: *Dendrobium tosaense* 'Makino'× *Dendrobium huoshanese* 'C.Z. Tang et S.J. Cheng'.
Variety denomination: 'YFY-HS1'.

FIELD OF THE INVENTION

This invention relates to a new and distinct variety of orchid plant, and more particularly to a hybrid of the Genus *Dendrobium.*

BACKGROUND AND DESCRPITION OF THE INVENTION

Nowadays, the Genus *Dendrobium* is considered to be one of the most precious Chinese herbs for treating ophthalmic defects. The Genus *Dendrobium* is a member of the Family Orchidaceae. The stem of the *Dendrobium* plant is the mainly medicinal part. Some Chinese medical codices disclose that the *Dendrobium* plant is the curative for some illnesses such as salivary defects, stomach defects, and ophthalmic defects.

It has been proved in U.S. patent application Ser. No. 10/648,651 that an extract of "DCMPbL6, 7D2H2" from the *Dendrobii Caulis* plant has the curative effects for the ophthalmic defects. However, since the *Dendrobii Caulis* usually has a slow growth property and its relevant resistance to the environment is poor, a plant having a fast growth nature and an abundant content of the extract of "DCMPbL6, 7D2H2" is desirous. After a long-term research, it's found that *Dendrobium huoshanese* C.Z. Tang et S.J. Cheng has the extract of "DCMPbL6, 7D2H2" but a slow growth rate, and *Dendrobium tosaense* Makino does not have the extract of "DCMPbL6, 7D2H2" but have a fast growth ability. In general, *Dendrobium huoshanese* C.Z. Tang et S.J. Cheng spreads on the border between Huoshan County, Anhui Province and Henan Province, China, and *Dendrobium tosaense* Makino spreads in Taiwan, Japan, and Guangxi Province, Yunnan Province and Guizhou Province, China.

After crossing *Dendrobium huoshanese* C.Z. Tang et S.J. Cheng (being the patrilineage) with *Dendrobium tosaense* Makino (being the matrilineage) via the normal crossing procedure, however, we discovered a new and distinctive *Dendrobium* plant (*Dendrobium tosaense* Makino× *Dendrobium huoshanese* C.Z. Tang et S.J. Cheng) with great growth vigor and high extract amount of "DCMPbL6, 7D2H2" in the cultivated field, and then we named it as 'YFY-HS1'.

The act of asexual reproduction of 'YFY-HS1' by normal tissue culture was performed by us in a controlled environment in I-Lan, Taiwan. The characteristics disclosed herein for 'YFY-HS1' were firm and were retained through the successive generations of asexual reproduction.

'YFY-HS1' is particularly characterized by its great growth vigor and the high extract amount of "DCMPbL6, 7D2H2" therefrom, so that 'YFY-HS1' has the apparent commercial value.

At present, 'YFY-HS1' is reproduced by the tissue culture, and cultivated in the greenhouses in Taiwan and Shanghai. 'YFY-HS1' has not been observed under all possible environmental conditions. It should be noted that the phenotype may vary significantly with variations in environment such as temperature, light intensity, fertilization, daylight etc. without any change in the genotype. The following observations and measurements describe the plant grown in I-Lan, Taiwan, under conditions, which approximate those generally used in commercial practice.

SPECIFIC DESCRIPTION OF THE PLANT

Please refer to Table 1, which shows some characteristics of the *Dendrobium huoshanese* C.Z. Tang et S.J. Cheng, the *Dendrobium tosaense* Makino and the 'YFY-HS1'.

Table 1. The partial characteristics of the *Dendrobium huoshanese* C.Z. Tang et S.J. Cheng, the *Dendrobium tosaense* Makino and the 'YFY-HS1'.

| Species | 'YFY-HS1' | *Dendrobium tosaense* Makino (the matrilineage) | *Dendrobium huoshanense* C. Z. Tang et S. J. Cheng (the patrilineage) |
|---|---|---|---|
| Stem Height | 20–35 cm | 25–45 cm | 8–12 cm |
| Dry weight/ per plant | 2–4 g | 5–8 g | 0.6–1.5 g |
| Flower shape# | Similar to the patrilineal | | |
| Growth type+ | Similar to the matrilineal | | |
| HPLC Profile* | Similar to the patrilineal | | |

Figure 3:
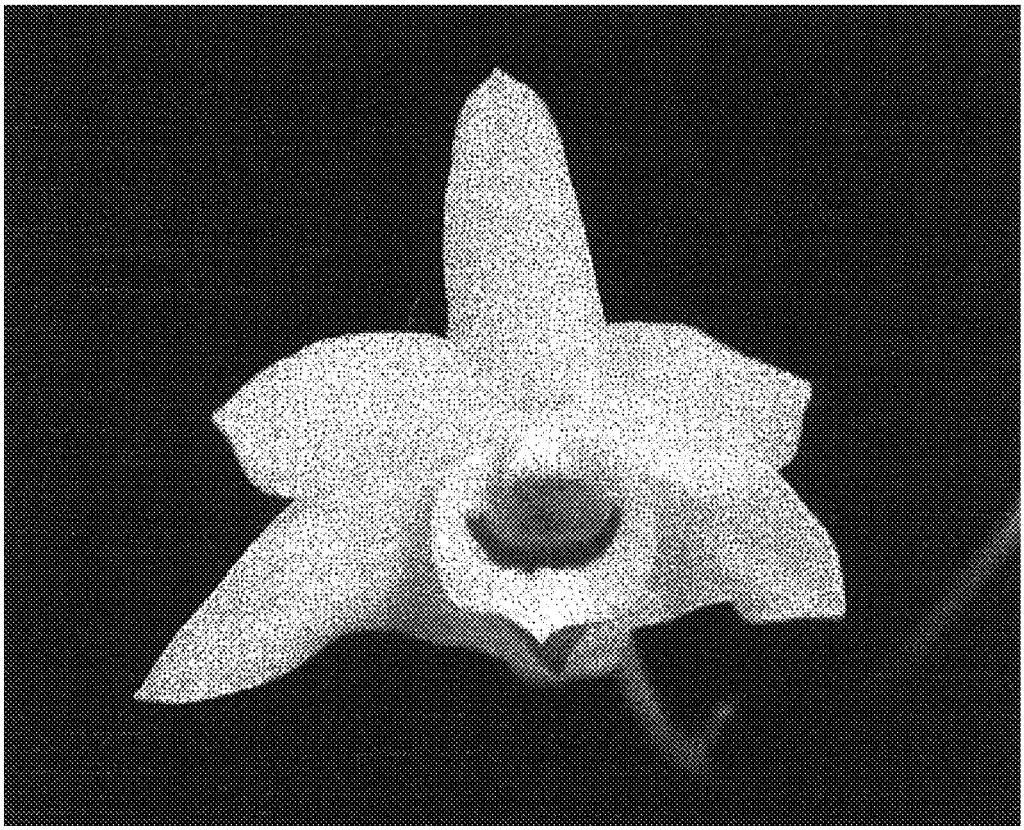
FIG. 3 show s the flower of the 'YFY-HS1'.
Figure 4:
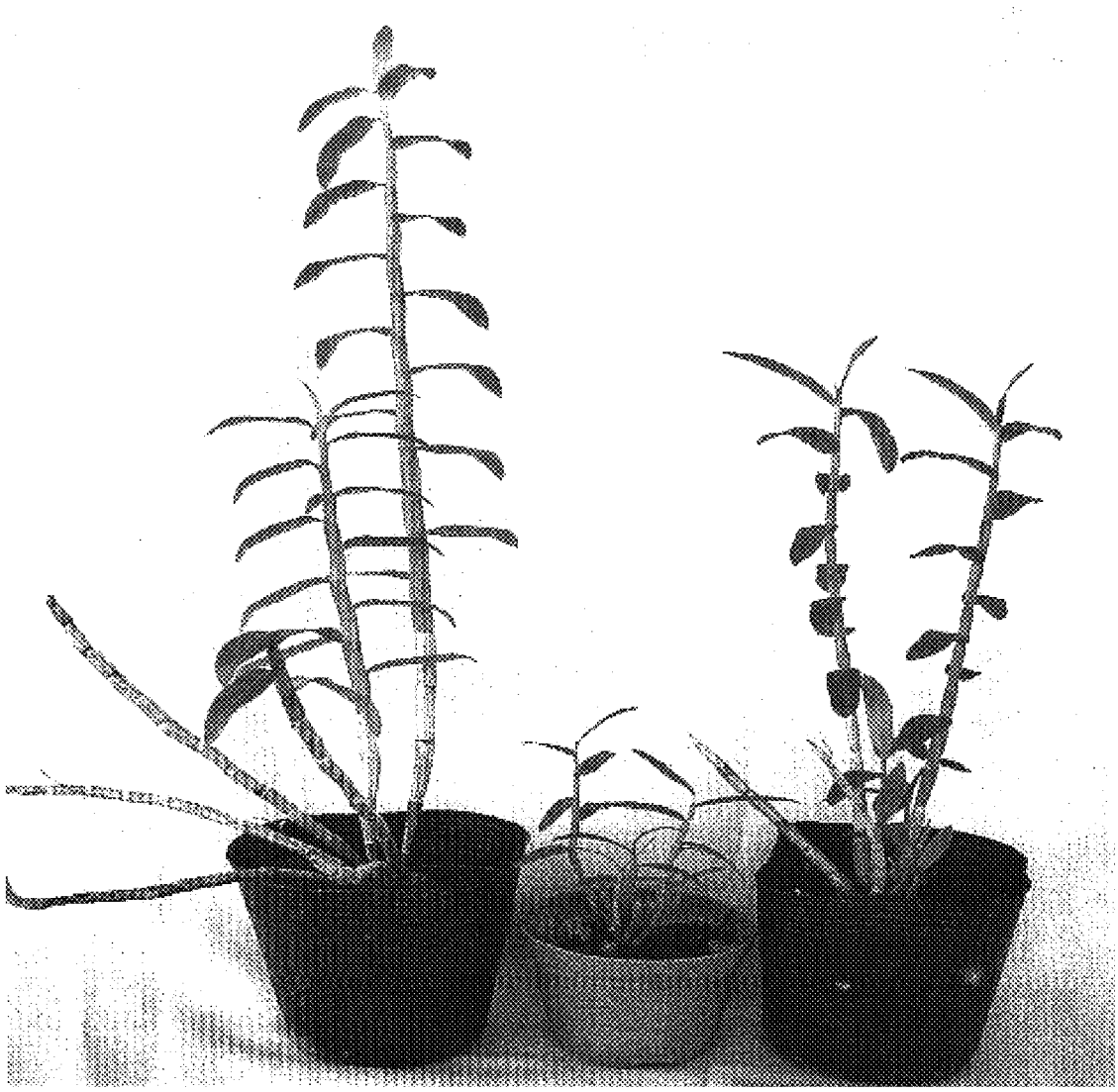
FIG. 4 shows the growth types of the matured *Dendrobium huoshanese* C.Z. Tang et S.J. Cheng, the matured *Dendrobium tosaense* Makino and the matured 'YFY-HS1'.
Figure 5:
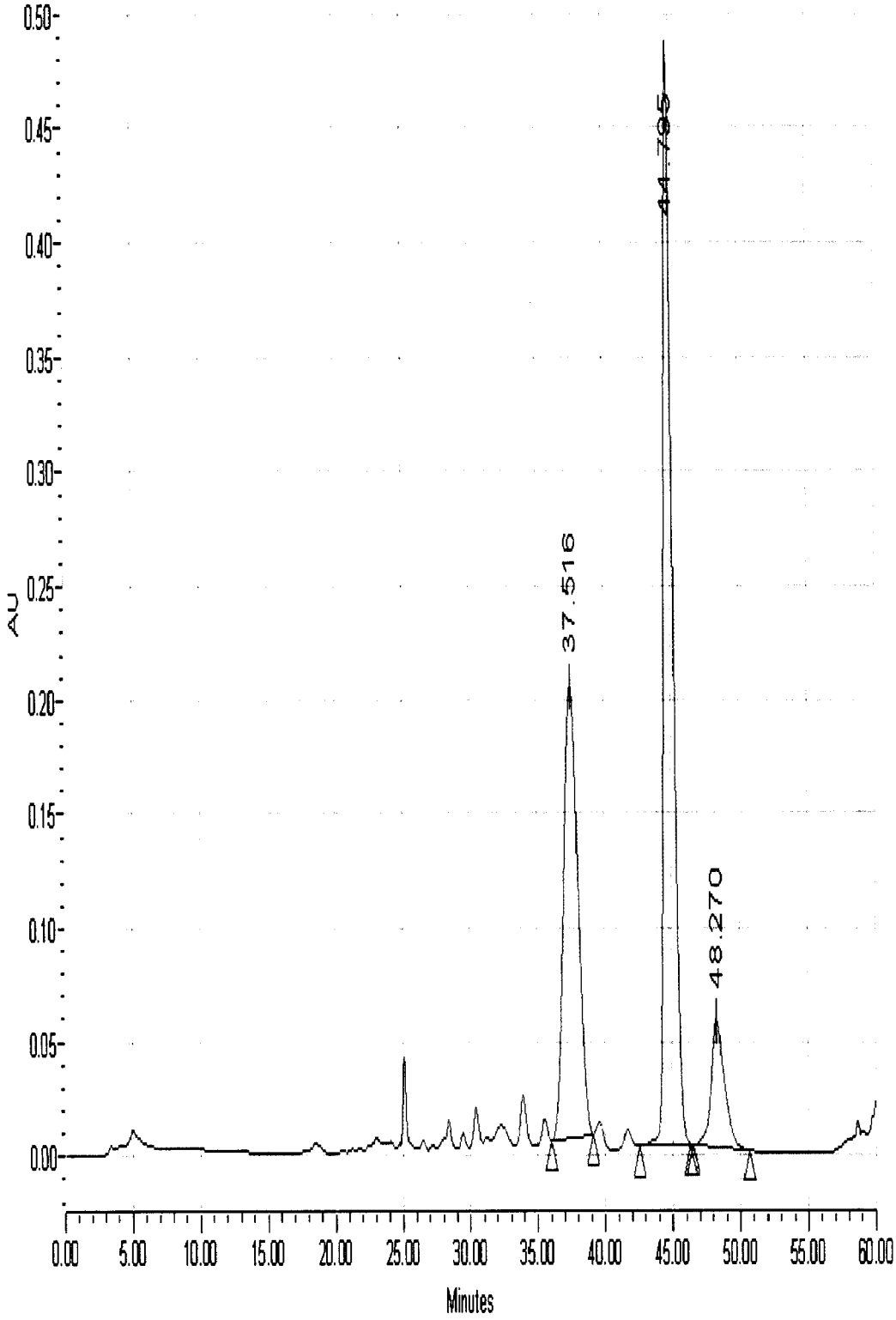
FIG. 5 shows the HPLC profile of the *Dendrobium tosaense* Makino.
Figure 6:
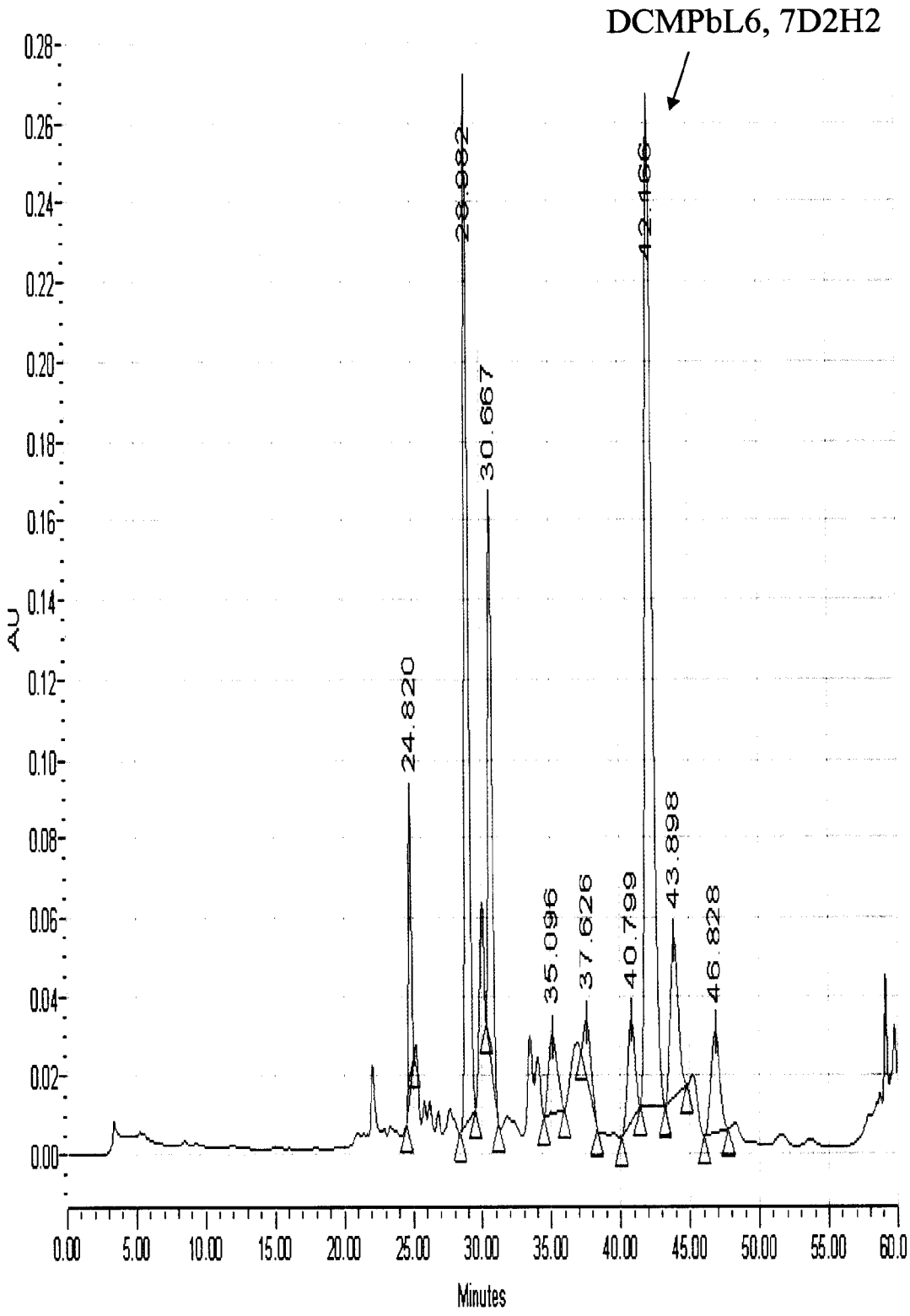
FIG. 6 shows the HPLC profile of the *Dendrobium huoshanese* C.Z. Tang et S.J. Cheng.
Figure 7:
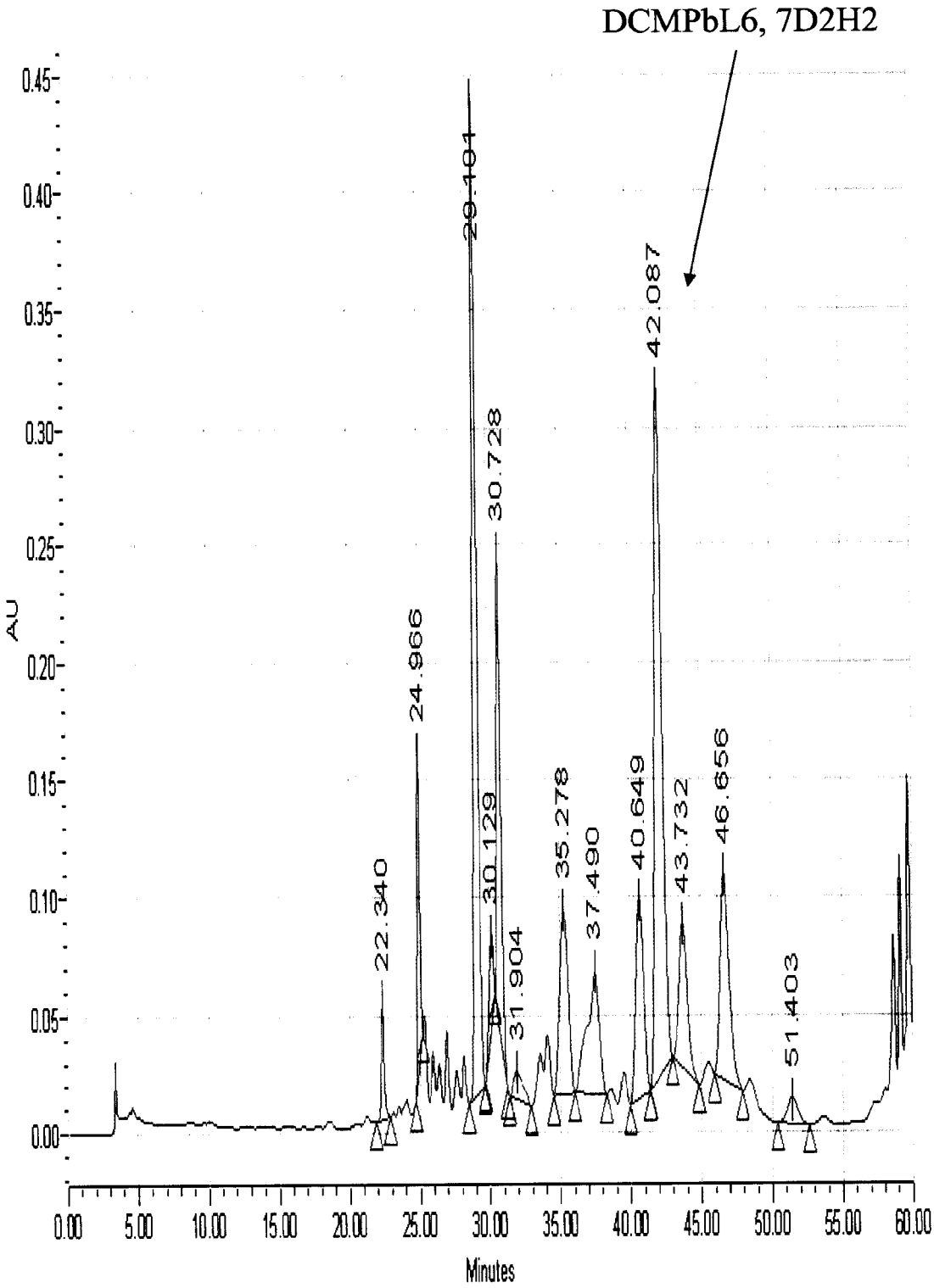
FIG. 7 shows the HPLC profile of the 'YFY-HS1'.

#, +The detailed could be found in the follow-up FIGS. 1–4.
*The detailed could be found in the follow-up FIGS. 5–7.

Figure 1:
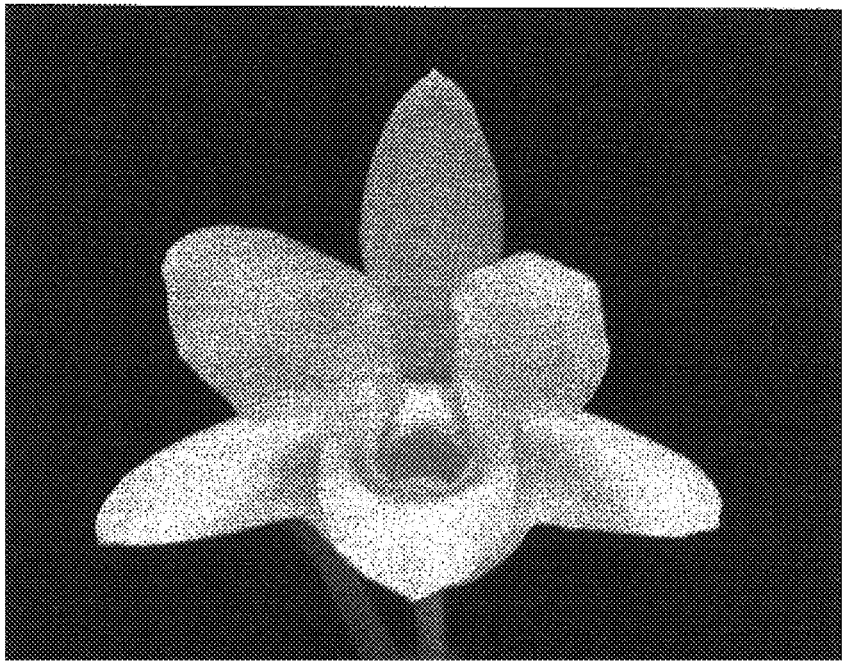
FIG. 1 shows the flower of the *Dendrobium huoshanese* C.Z. Tang et S.J. Cheng.
Figure 2:
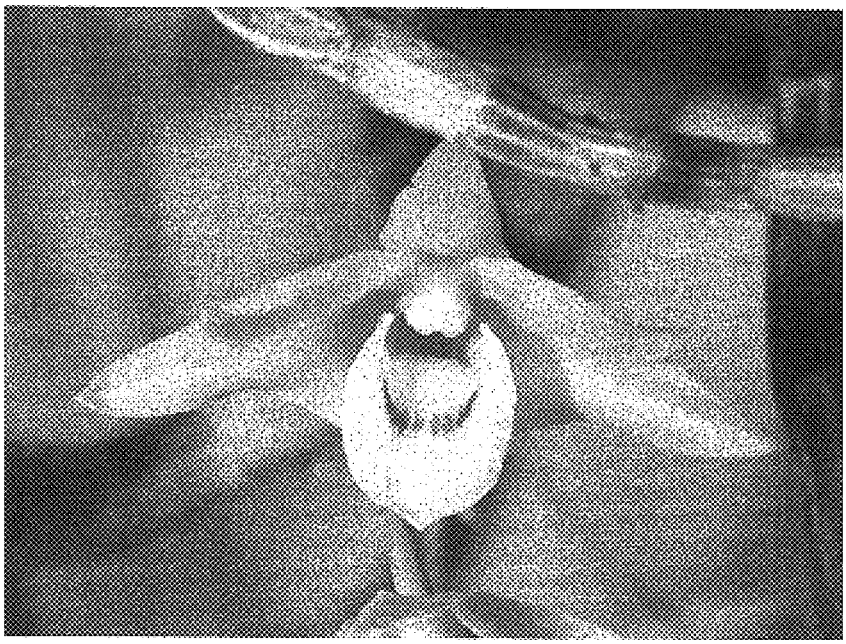
FIG. 2 shows the flower of the *Dendrobium tosaense* Makino.

Please refer to FIGS. 1–3, which respectively show the flowers of the *Dendrobium huoshanese* C.Z. Tang et S.J. Cheng, the *Dendrobium tosaense* Makino and the 'YFY-HS1'. As shown in FIGS. 1–3, the flower shape of the 'YFY-HS1' is similar to that of the *Dendrobium huoshanese* C.Z. Tang et S.J. Cheng, but the relevant color layouts are different.

Please refer to FIG. 4, which shows the growth types of the matured *Dendrobium huoshanese* C.Z. Tang et S.J. Cheng, the matured *Dendrobium tosaense* Makino and the matured 'YFY-HS1'. After being cultured for about 18 months, it's found, as shown in FIG. 4, the growth type of the 'YFY-HS1' is more similar to that of the *Dendrobium huoshanese* C.Z. Tang et S.J. Cheng than that of the *Dendrobium tosaense* Makino.

Please refer to FIGS. 5–7, which respectively show the HPLC profiles of the *Dendrobium tosaense* Makino, the *Dendrobium huoshanese* C.Z. Tang et S.J. Cheng and the 'YFY-HS1'. The relevant analyzing conditions are:

IINSTRUMENT: Waters HPLC (WATERS 600)

COLUMN: VERCORPAK Inertsil 5 ODS-2 4.6×150 mm

FLUENT: A 0.1% Acetic acid

B 100% MeOH

GRADIENT: A/B 80/20 → 45/55

FLOW RATE: 1–0.6 ml/min

WAVELENGTH: 337 nm

INJECTION: 100 μl

As shown in FIGS. 5–7, the extract of "DCMPbL6, 7D2H2" (the chromatographic peaks appear at about 42 minute) is indeed contained in the *Dendrobium huoshanese* C.Z. Tang et S.J. Cheng and the 'YFY-HS1'.

Through the above descriptions, a new and distinct *Dendrobium* plant named 'YFY-HS1' does have been provided.

The chart used in the identification of the colors is PANTONE Professional Color System. The age of the observed plant is 18 months from planting.

Origin: Seedling from a cross between the *Dendrobrium tosaense* Makino and *Dendrobium huoshanense* C.Z. Tang et S.J. Cheng.

Parentage:

*Patrulineal parent.*—*Dendrobrium huoshanense* C.Z. Tang et S.J. Cheng.

*Matrilineal parent.*—*Dendrobrium tosaense* Makino.

Classification: *Dendrobium* hybrid.

Propagation: Asexual propagation by tissue culture.

Plant:

*Size.*—A mature plant is tufted and has a height of approximately 20–35 cm and average plant spread of 15–30 cm.

*Growth habit.*—Preferring a moisture environment, and growing well under 20–30° C.

*Flowers per flowering stem.*—Approximately 2 to 5.

*Stems.*—Tufted, erect, terete, 20–35 cm in height, 4–7.5 mm in diameter, somewhat slender towards the base.

*Color of stem.*—Fern (Pantone 16-0430), Paridot (Pantone 17-0336), Grasshopper (Pantone 18-0332) and Calliste Green (Pantone 18-0324); and with some spots in Red Plum (Pantone 19-2025) and Mauvewood (Pantone 17-1522) on the stem's surface.

*Stem's surface texture.*—The stem's surface is tightly covered by the membranous leaf sheath having vertical fiber lines.

Leaf:

*General shape.*—Oblong-lanceolate.

*Shape of tip.*—Acute to sub-obtuse.

*Direction of leaf.*—Alternate.

*Length.*—3.5–6 cm.

*Width.*—1.2–1.5 cm.

*Color of leaf surface.*—Artichoke Green (Pantone 18-0125), Elm Green (Pantone 18-0121), Vineyard Green (Pantone 18-0117), Bronze Green (Pantone 18-0317), Chive (Pantone 19-0323).

*Underside color.*—Elm Green (Pantone 18-0121), Vineyard Green (Pantone 18-0117), Paridot (Pantone 17-0336), Turtle Green (Pantone 17-0330), Grasshopper (Pantone 18-0332), Calliste Green (Pantone 18-0324).

*Leaf surface texture.*—Thin-leathery.

*Thickness.*—0.1–0.2 cm.

*Variegation.*—None.

*Sheath.*—Membranous, no petiole.

*Color of sheath.*—Silver Lining (Pantone 14-4501) with some spots in Red Plum (Pantone 19-2025) and Mauvewood (Pantone 17-1522) in young sheaths, and Aluminum (Pantone 16-1107) in old sheaths.

Flowers:

*Inflorescence.*—Racemes, born on the upper nodes, 2–4 cm in length.

*Flower.*—2–2.5 cm in length, 2.5–3.0 cm in width.

Sepals:

*Upper sepal.*—Ovate-oblong, 1.0–1.4 cm in length, 0.4–0.6 cm in width.

*Color of upper sepal.*—Antique White (Pantone 11-0105), Winter White (Pantone 11-0507).

*Number of upper sepal.*—1.

*Lateral sepal.*—Obliquely triangular and somewhat sub-obtuse, 1.0–1.4 cm in length, 0.5–0.8 cm in width.

*Color of lateral sepal.*—Antique White (Pantone 11-0105), Winter White (Pantone 11-0507).

*Number of lateral sepal.*—2.

*Petal.*—Elliptic, 1.3–1.7 cm in length, 0.6–0.8 cm in width.

*Petal numbers.*—2.

*Petal shape.*—Long elliptic.

*Lip shape and texture.*—Somewhat wide-rhombate, 1.3–1.7 cm in length, 1.3–1.7 cm in width, inner surface has a central disc with Raffia (Pantone 13-0725) or Cream Gold (Pantone 13-0739) fleshy elevation, extending forwards with one transverse Red Plum (Pantone 19-2025) and Mauvewood (Pantone 17-1522) band.

*Color of lip.*—Antique White (Pantone 11-0105) and Winter White (Pantone 11-0507) in outer surface; Raffia (Pantone 13-0725) or Cream Gold (Pantone 13-0739) in inner surface.

*Color of flower.*—Antique White (Pantone 11-0105), Winter White (Pantone 11-0507).

*Column.*—3.0–5.0 mm in length, 0.8–1.0 cm in width, column-foot curved, with Red Plum (Pantone 19-2025) and Mauvewood (Pantone 17-1522) spots inside.

*Anther cap.*—Antique White (Pantone 11-0105).

*Pollen color.*—Dandelion (Pantone 13-0758), Lemon (Pantone 13-0752), and Maize (Pantone 13-0746).

*Pollen size.*—About less than 0.5 mm in width and about 1 mm in length.

*Bloom period.*—7–14 days.

*Fragrance.*—Delicate fragrance.

*Flowering time.*—April to June.

Pseudobulb: None.

Reproduction organs:

*Pollinia.*—4 in numbers; color: Dandelion (Pantone 13-0758), Lemon (Pantone 13-0752), and Maize (Pantone 13-0746).

*Pedicel.*—2–3 cm in length; color: Fern (Pantone 16-0430), Green Oasis (Pantone 15-0538).

Disease resistance: No specific resistance.

Insect resistance: No specific resistance.

It is claimed:

1. A new and distinct variety of *Dendrobium* plant named as 'YFY-HS1' having the characteristics herein illustrated and described.

* * * * *

*Dendrobium tosaense Makino*

*Dendrobium huoshanense C.Z. Tang et S.J. Cheng* 'YFY-HS1'